United States Patent [19]

Noel

[11] Patent Number: 5,328,696
[45] Date of Patent: Jul. 12, 1994

[54] DEVICES USING SILICONE PRESSURE SENSITIVE ADHESIVES CONTAINING ORGANIC WAX

[75] Inventor: Ross A. Noel, Midland, Mich.

[73] Assignee: Dow Corning Corporation, Midland, Mich.

[21] Appl. No.: 733,567

[22] Filed: Jul. 22, 1991

[51] Int. Cl.⁵ .............................................. A61F 13/00
[52] U.S. Cl. .................................... 424/449; 424/448; 524/277; 524/487; 525/478
[58] Field of Search ............... 420/448, 449; 524/487, 524/277; 525/478

[56] References Cited

U.S. PATENT DOCUMENTS

| | | | |
|---|---|---|---|
| 2,807,554 | 9/1957 | Serey | 524/277 |
| 3,857,720 | 12/1974 | Fellows | 524/277 |
| 3,983,298 | 9/1976 | Hahn | 525/478 |
| 4,404,035 | 9/1983 | Ona | 524/277 |
| 4,559,054 | 12/1985 | Bruck | 424/449 |
| 4,837,027 | 6/1989 | Lee | 424/449 |
| 4,925,671 | 5/1990 | Abber | 424/449 |
| 4,942,037 | 7/1990 | Bondi | 424/448 |
| 4,990,561 | 2/1991 | Yoshioka | 524/763 |
| 5,006,342 | 4/1991 | Chang | 424/447 |
| 5,133,972 | 7/1992 | Ferrini et al. | 424/469 |

*Primary Examiner*—D. Gabrielle Phelan
*Attorney, Agent, or Firm*—Cargill and Bliss

[57] ABSTRACT

Hot-melt silicone pressure sensitive adhesive compositions containing organic waxes, methods of using the compositions and devices made using the compositions are disclosed. The hot-melt silicone pressure sensitive adhesive compositions include a mixture of (i) a silicate resin, (ii) a silicone fluid, and (iii) an organic wax having a melting point of between 30° C. and 150° C. The organic wax decreases dynamic viscosity of the adhesive at temperatures equal to or below about 200° C.

10 Claims, 1 Drawing Sheet

DEVICES USING SILICONE PRESSURE SENSITIVE ADHESIVES CONTAINING ORGANIC WAX

TECHNICAL FIELD

The present invention relates to hot-melt silicone pressure sensitive adhesive compositions containing organic wax, methods of using the composition, and devices made using the composition.

BACKGROUND OF THE INVENTION

A pressure sensitive adhesive, generally, is a material which adheres to a surface with slight pressure and releases from the surface with negligible transfer of the material to the surface. Silicone pressure sensitive adhesives that are known in the art are typically solvent-based adhesives. The solvents are employed primarily to reduce the viscosity of the silicone pressure sensitive adhesive to a viscosity which is easily coated onto the substrate of choice, and the solvents are removed after coating. As with any solvent-based pressure sensitive adhesive (PSA), special precautions must be taken to contain and avoid environmental exposure of the solvents and avoid flammable and explosive conditions as many of the solvents used are flammable.

Hot-melt pressure sensitive adhesives are those adhesives, which upon heating, melt to viscosities suitable for coating, but when cooled are generally in a flowless state. Hot-melt pressure sensitive adhesives exhibit the following advantages over solvent-based pressure sensitive adhesives. Hot-melt pressure sensitive adhesives: (1) do not require removal and containment of solvents; (2) due to the absence of flammable solvents, do not require special precautions to avoid fires; (3) make available coating processes other than those commonly used with solvent-based pressure sensitive adhesives; and (4) are more easily coated into thick sections with minimal bubbling, a problem which often results with coating out solvent based PSA's. In addition, hot-melt PSA's have the advantage of not containing solvents which sometimes interfere with the addition of other ingredients to the PSA.

Silicone pressure sensitive adhesives are preferred over other types of PSA's in many applications, especially in the medical area. For example, because silicone pressure sensitive adhesives are acceptable for topical use, these have found use in transdermal drug delivery applications which involve the adherence of a drug-containing patch to a patient's skin.

U.S. Pat. No. 4,865,920 to Randall P. Sweet, discloses a method of making hot-melt silicone pressure sensitive adhesives which have the inherent benefits of being composed of silicone and being a hot-melt PSA. In U.S. Pat. No. 4,865,920, the hot-melt silicone pressure adhesive composition consists of (i) a silicate resin; (ii) a silicone fluid; and (iii) 1 to 10 weight percent, based on the total weight of the silicate resin and silicone fluid, of an ester having the formula: R—C(O)OR' wherein R is a monovalent hydrocarbon radical having from 2 to 32 carbon atoms and R' is a monovalent hydrocarbon radical having from 1 to 14 carbon atoms.

Although this silicone pressure sensitive adhesive composition has been found to be highly efficacious, it is desirable to include organic waxes that decrease viscosity and improve of the coatability of the hot-melt adhesive at temperatures at or below 200° C.

It is desirable that the adhesive be compatible with a variety of release liners. The new hot-melt silicone pressure sensitive adhesive must allow permeation of lipophilic drugs through the PSA. Also, the adhesive should have controllable adhesion, so that the aggressiveness of adhesion can be tailored to the application.

SUMMARY OF THE INVENTION

This invention provides a hot-melt pressure sensitive adhesive composition which is formed of materials which are highly acceptable in topical applications. The hot-melt silicone pressure sensitive adhesive compositions of this invention contain an organic wax which renders the adhesive less viscous at temperatures up to about 200° C. and therefore improves adhesive coatability over the prior art silicone PSA's and the hot-melt PSA of U.S. Pat. No. 4,865,920. The invention also provides a means of controlling the pressure sensitive adhesive properties of tack, adhesion, and release of the composition.

The hot-melt silicone pressure sensitive adhesive composition comprises a mixture of (i) a silicate resin and (ii) a silicone fluid, the mixture exhibiting tackiness and adhesiveness, the mixture being blended with (iii) an organic wax having a melting point between about 30° C. and 150° C., and which decreases the dynamic viscosity of the adhesive at temperatures equal to or below 200° C. Improved adhesive coatability, minimizes waste of materials during manufacture and expedites production. This results in cost savings and increases profits. The invention also encompasses methods of using the composition, and devices made using the compositions.

DETAILED DESCRIPTION OF THE INVENTION

Figure 1:
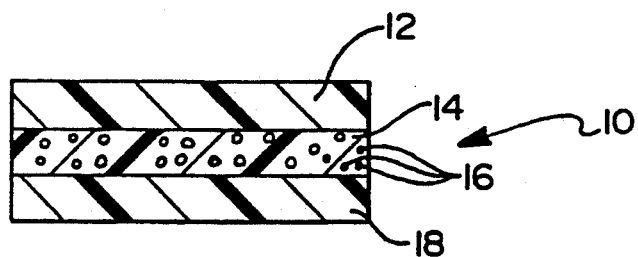
FIG. 1 shows a matrix-type delivery device for a bioactive agent or drug in place within a transdermal patch.

Generally, the hot-melt compositions of the invention are composed of a silicone pressure sensitive adhesive containing (i) a silicate resin present in an amount between about 30 to about 70 percent by weight based on total composition weight; (ii) a silicone fluid present in an amount between about 22 to about 60 percent by weight based on total composition weight; and (iii) an organic wax present in an amount between about 1.0 to about 25.0 percent by weight based on total composition weight.

The following paragraphs disclose acceptable and preferable silicone pressure sensitive adhesives which may be combined with the disclosed organic waxes to provide an improved hot-melt adhesive combination with decreased dynamic viscosity. This improved adhesive may be used, in turn, to form improved devices for many applications including transdermal drug delivery patches and other medical applications which do not require solvents for coating the adhesive.

As mentioned above, hot-melt PSA's are preferred over other adhesives because no solvents are required to coat the adhesive on a substrate (e.g. a bandage or patch). It appears that the addition of organic waxes to a basic silicone PSA formulation helps to decrease dynamic viscosity and allows it to be hot melt coated. This means that the coatability of the PSA is improved in the absence of solvents and better devices can be made. One of ordinary skill in the art will clearly see the advantages of the present invention.

I. Suitable Silicone Pressure Sensitive Adhesives

One suitable class of pressure sensitive adhesives to be employed in the hot-melt compositions of this invention consists of a mixture of (i) a trimethylsilyl-endblocked polysilicate resin such as a silicate resin, consisting of a benzene-soluble resinous copolymer containing silicon-bonded hydroxyl radicals and consisting essentially of triorganosiloxy units of the formula $R_3SiO_{\frac{1}{2}}$ and tetra functional siloxy units of the formula $SiO_{4/2}$ in a ratio of about 0.6 to 0.9 triorganosiloxy units for each tetra functional siloxy unit present in the copolymer, wherein each R is a monovalent organic radical independently selected from the group consisting of hydrocarbon radicals of from 1 to 6 inclusive carbon atoms; and (ii) a silanol-endstopped polydiorganosiloxane fluid, e.g. a polydimethylsiloxane fluid. U.S. Pat. No. 2,736,721 to Dexter, et al. and U.S. Pat. No. 2,814,601, to Currie, et al. are hereby incorporated by reference to teach of such or similar pressure sensitive adhesive compositions.

Another class of suitable pressure sensitive adhesives for use in combining with the organic wax according to the present invention is that or those similar to U.S. Pat. No. 2,857,356, to Goodwin, Jr., which is hereby incorporated by reference. The Goodwin, Jr. patent teaches silicone pressure sensitive adhesives which consist of a mixture of ingredients comprising (i) a cohydrolysis product of a trialkyl hydrolyzable silane and alkyl silicate, wherein the cohydrolysis product contains a plurality of silicon-bonded hydroxy groups, and (ii) a linear, high viscosity organopolysiloxane fluid containing silicon-bonded hydroxy groups.

To practice the present invention the silicate resin (i) and the silicone fluid (ii) may optionally be condensed together according to a procedure such as the procedure described in Canadian Patent 711,756 to Pail, which patent is hereby incorporated by reference. In such a condensation reaction, the silicate resin (i) and the silicone fluid (ii) are mixed together in the presence of a catalytic amount of a silanol condensation catalyst, and then the silicate resin (i) and the silicone fluid (ii) are condensed, for example, by heating under reflux conditions for 1 to 20 hours. Examples of silanol condensation catalysts are primary, secondary, and tertiary amines, carboxylic acids of these amines and quaternary ammonium salts.

Another class of suitable pressure sensitive adhesives to use in combination with the organic waxes are those compositions described in U.S. Pat. Nos. 4,591,622 and 4,584,355 to Blizzard et al., U.S Pat. No. 4,585,836 to Homan et al., and U.S. Pat. No. 4,655,767 to Woodard et al., which patents are also hereby incorporated by reference. Generally, these pressure sensitive adhesives consist of a blend of (i) a silicate resin and (ii) a silicone fluid which are chemically treated to reduce the silicone bonded hydroxyl content of the blend. These adhesives may optionally be condensed as described immediately above prior to the chemical treatment.

Typically, the most practical pressure sensitive adhesive, to combine with an organic wax, contains between about 200 ppm and 1,200 ppm of silanol radicals, and includes a silicate resin combined with a silicone fluid as described above. The silicate resin preferably has a molecular weight ranging from about 3,500 to about 7,000, and is employed in amounts from about 40 to about 70 percent by weight based on the total resultant composition of the silicone pressure sensitive adhesive. The silicone fluid is preferably employed from about 30 to about 60 percent by weight, wherein the total silicate resin and silicone fluid equal 100 percent by weight.

The silicone pressure sensitive adhesives used in this invention are not considered to be "silicone rubbers", which generally refer to non-tacky vulcanized rubbers. The most common type of silicone rubber consists of a mixture of a polydimethylsiloxane gum, a filler (such as fumed silica or other inorganic, non-resinous material), or a crosslinker, and optionally, a catalyst. On the other hand, the silicone pressure sensitive adhesives employed in this invention are tacky (or sticky) to the touch without the addition of plasticizers and typically adhere to a substrate after mild pressure is applied. The silicone pressure sensitive adhesives may be cured or "rubberized" after being mixed with a cohesive strengthening agent as discussed below. However, even after curing, the silicone pressure sensitive adhesive composition remains tacky.

The process of curing or crosslinking silicone pressure sensitive adhesives is known in the art. For example, see "Silicone Pressure Sensitive Adhesives" by D. f. Merrill in the *Handbook Of Pressure Sensitive Adhesive Technology*, edited by D. Satas (Van Nostrand Reinhold, Florence, Kentucky, 1982), pages 344–352 and "Formulating Silicone Pressure Sensitive Adhesives For Application Performances" by L. A. Sobieski in *Making It Stick in '86, Advances In Pressure Sensitive Tape Technology*, seminar proceedings (Pressure Sensitive Tape Council, Deerfield, Illinois, 1986), pages 1–5, both sources being hereby incorporated by reference.

Generally, however, for drug delivery applications, the silicone pressure sensitive adhesive compositions are not crosslinked because either (1) the crosslinking temperature is too high for the drugs or (2) the additives needed for crosslinking are non-biocompatible ingredients. A silicone pressure sensitive adhesive composition is generally considered not crosslinked if it can be dissolved in a solvent.

Another difference between silicone pressure sensitive adhesives suitable for use in the present invention and silicone rubbers which are unsuitable, lies in the fact that silicone pressure sensitive adhesives are usually fillerless or contain low amounts, e.g., less than about 5 weight percent, of fillers, such as fumed silica or other inorganic reinforcing fillers known in the silicone art. On the other hand, silicone rubbers typically contain about 15–35 weight percent filler. Fillers are usually not desired in high quantities in silicone pressure sensitive adhesives, because high quantities often cause the silicone pressure sensitive adhesives to lose tack and adhesiveness and to increase in viscosity, making it more difficult to apply a coating of the silicone pressure sensitive adhesive. In addition, the non-permeable silicas reduce the permeability of the adhesive.

The silicone PSA's described above are all suitable for combining with certain organic waxes, as described in the following paragraphs. These organic waxes, when combined with the PSA's provide adhesives which exhibit decreased dynamic viscosity, and improved coatability without solvents.

II. The Organic Waxes

The organic waxes of the present invention include waxes having a melting point between 30° C. and 150° C., and include 1) mineral waxes such as ozokerite, ceresine and paraffin, 2) vegetable waxes such as candelilla and carnauba, 3) animal waxes such as beeswax, and 4) mixtures thereof.

Preferably, the organic wax is added in an amount between about 1.0 and about 25.0 percent by weight based on total composition weight. Best results are noted when the wax is utilized in an amount between about 5 percent and about 20 percent by weight based on total composition and especially when the wax is present in an amount between about 5 and about 15 percent by weight based on total composition weight.

The organic wax functions to decrease the dynamic viscosity of the hot-melt pressure sensitive adhesive at temperatures equal to or below about 200° C. Desirable dynamic viscosities of the wax-containing adhesives, are less than or equal to 800 poise at temperatures of about 200° C. The wax is particularly effective at temperatures of between about 85° C. and 200° C. to improve the coatability of the adhesive onto a substrate. This effect is shown in Examples 1–3.

The hot-melt silicone pressure sensitive adhesive compositions described herein are prepared by mixing silicate resin (i) and silicone fluid (ii) with (iii) the organic wax at a temperature of at least 85° C. Alternatively, the wax may be dissolved in solvent added to the silicate resin and fluid mixture and thereafter the solvent is removed from the mixture. The hot-melt silicone pressure sensitive adhesive compositions are then heated to a coatable viscosity, to temperatures of between about 85° C. and 200° C., and coated on a substrate. The adhesive coated substrate is then cooled until it is in a non-flowing state.

The hot-melt silicone pressure sensitive adhesive compositions are applied to a substrate, or other backing, by using any conventional means, such as roller coating, dip coating, extrusion, knife coating, or spray coating. Although the hot-melt silicone pressure sensitive adhesive compositions of the invention are preferably adhered to a bandage or patch for medical applications, they will also adhere to many substrates, such as paper, cloth, glass cloth, silicone rubber, polyethylene, polyethylene terephthalate, polytetrafluoroethylene, glass, wood, metals, and skin. Therefore, the following suggested uses and examples should not be used to limit the invention. Depending on the desired use, it may be desirable to apply adhesion promoters on the substrate surface upon which the hot-melt silicone pressure sensitive adhesive composition will be placed.

As is known to one skilled in the art, hot-melt silicone pressure sensitive adhesive compositions such as those used in this invention, are especially suitable for assisting in delivering bioactive agents, usually drugs, to a bioactive agent-accepting substrate, such as a patient's skin. The hot-melt silicone pressure sensitive adhesive compositions of this invention may be employed in three types of bioactive agent delivery devices, as described herein below.

III. Devices Utilizing Adhesive

The hot-melt silicone pressure sensitive adhesive compositions of this invention are especially suitable for assisting in delivering a bioactive agent, such as a drug, to a bioactive agent-accepting substrate, such as a patient's skin. The hot-melt silicone pressure sensitive adhesive compositions of this invention may be employed in three types of bioactive agent delivery modes.

The first mode is a matrix-type of delivery device for a bioactive agent or drug. As shown in FIG. 1, device 10 comprises three layers, including a backing substrate 12 which may be permeable or occlusive to water vapor transmission from skin; a matrix 14, which may be between about 1 and about 15 mils thick, atop at least portions of the backing substrate and containing a silicone pressure sensitive adhesive, said adhesive including drugs, excipients or co-solvents 16, said adhesive being compatible with the drugs, excipients or co-solvents; and a pressure sensitive adhesive release liner 18.

The matrix-type transdermal drug delivery device as shown in FIG. 1 may include various drugs selected from the group consisting of cardiovascular agents, antiarrhythmic agents, antianginal agents, antibiotics, antifungals, antimicrobials, antihypertensives, analgesics, local anesthetics, contraceptives, hormonal supplements, anti-smoking agents, appetite suppressants, hypnotics, and anxiolytics.

Figure 2:
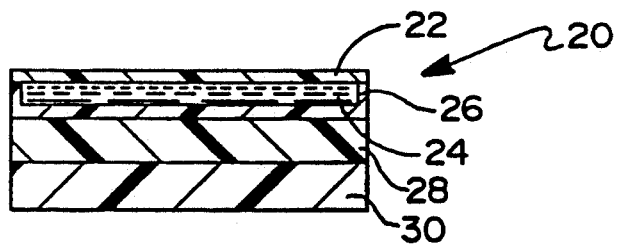
FIG. 2 shows a liquid reservoir-type transdermal drug delivery device.

As shown in FIG. 2, the second mode of delivery is a reservoir-type transdermal drug delivery device. FIG. 2 shows a liquid containing reservoir-type drug delivery device, generally denoted as numeral 20, which comprises a minimum of five layers from top to bottom. The first layer 22 is a backing substrate. The second layer includes a liquid reservoir 24 which may contain bioactive agents or other compositions selected from the group consisting of drugs, excipients and co-solvents. The third layer 26 is a rate controlling membrane positioned such that the reservoir 24 is sealed between the backing substrate 22 and the rate controlling membrane 26. This membrane acts as the rate controlling mechanism for the delivery of the liquid from the reservoir 24 to the patient. The fourth layer 28 is a hot-melt, organic wax-containing pressure sensitive adhesive coated on top of the previous layers, and the adhesive should be compatible with any of the drugs, excipients and co-solvents present in the liquid reservoir. The fifth layer 30 is a release liner attached on top of the adhesive layer, averaging between about 1 and 15 mils thick and preferably between about 1 and 3 mils thick. The device allows the bioactive agent of liquid reservoir 24 to pass from the reservoir through the attached rate controlling membrane 26 and adhesive layer 28 into the skin of the patient. The reservoir 24 of the transdermal drug delivery device may include drugs selected from the group consisting of cardiovascular agents, antiarrhythmic agents, antianginal agents, antibiotics, antifungals, antimicrobials, antihypertensives, analgesics, local anesthetics, contraceptives, hormonal supplements, anti-smoking agents, appetite suppressants, hypnotics, and anxiolytics.

Figure 3:
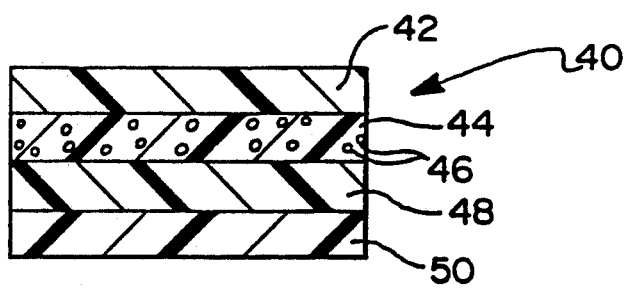
FIG. 3 shows a solid state reservoir-type transdermal drug delivery device.

The third mode of delivery is a solid state reservoir transdermal drug delivery device denoted by numeral 40, shown in FIG. 3. This device includes a first layer 42 which is a backing substrate. The second layer constitutes a solid reservoir 44 which may contain one or more bioactive agents or other compositions selected from the group consisting of drugs, excipients and co-solvents indicated as 46. The third layer is a hot-melt organic wax-containing pressure sensitive adhesive layer 48 which is compatible with the drugs, excipients and co-solvents contained therein. The pressure sensitive adhesive layer averages between 1 and 15 mils thick, and preferably between 1 and 3 mils thick. The fourth layer is a release liner 50. An additional layer (not shown) comprising a rate controlling membrane may be positioned between the solid reservoir 44 and the pressure sensitive adhesive layer 48. Solid reservoir 44 may contain drugs as described above for the liquid reservoir device of FIG. 2.

The adhesive layer of each of the matrix-type and reservoir-types of delivery device may include one or a combination of co-solvents and excipients which increase solubility of the drug in the adhesive matrix, enhance skin permeation to the drug, or enhance drug release from the system. These co-solvents and excipients may include fatty acid esters, polyols, surfactants, terpenes, glycerol esters, polyethylene glycol esters, amides, sulfoxides, lactams, nonionic surfactants, sorbitan esters, or a combination of more than one co-solvent or excipient.

The following examples of the invention are meant to be illustrative only and should not be construed as limiting the invention which is properly delineated in the appended claims. In the following examples, all parts and percentages are by weight unless otherwise specified.

IV. Examples

The below described basic silicone pressure sensitive adhesives, I, II, and III were prepared without the organic waxes as called for by the present invention. These are indicted in the Examples as the control samples, Control PSA I, Control PSA II, and Control PSA III. Once these basic formulations were prepared, examples were made by adding various organic waxes, testing them and tabulating the results.

The basic adhesive formulations included two main components: a silicate resin and a silicone fluid. We will be discussing Adhesives I, II, and III which were made from various combinations of Resins A-1, A-2 and trimethylsiloxy endblocked polydimethylsiloxane (PDMS) Fluid A as described below.

For the following examples, Resin A-1 is a xylene solution of a resinous copolymeric siloxane prepared from 45 parts of sodium silicate (41.6° Be) and 20 parts of $Me_3SiCl$ ($Me=CH_3$) according to the method of U.S. Pat. No. 2,676,182 to Daudt, et al., which is hereby incorporated by reference, and contains $Me_3SiO_{\frac{1}{2}}$ units and $SiO_{4/2}$ units in a ratio of approximately 0.75:1.0, and has a non-volatile content (N.V.C.) of typically about 69-71%, an acid number in the range of 0.3 to 1.4, a viscosity value in the range of 10-14 centipoise at 25° C. at 60% N.V.C. in xylene solution, and a silicon-bonded hydroxyl content of about 2.5 weight percent based on a 100% N.V.C.

Resin A-2 is devolatilized Resin A-1 (100% non-volatile content).

PDMS Fluid A is a homogeneous mixture of a hydroxyl-endblocked polydimethylsiloxane having a number-average molecular weight of approximately 40,000, along with minor amounts of cyclic polydimethylsiloxane having degrees of polymerization between 4 and 30, the mixture having a viscosity between 12,000 and 15,000 centipoise as measured using a Brookfield Viscometer Model HAF with spindle #3 at 10 RPM's.

Control PSA I was prepared by homogeneously mixing 24.1 parts by weight of Resin A-2, 39.8 parts by weight xylene, and 36.1 parts by weight PDMS Fluid A. The mixture was then heated to 115° C. and anhydrous ammonia was passed through the mixture at a rate of 11 ml/min/lb of non-volatile component of the mixture for approximately 4 hours. To endcap the mixture, hexamethyldisilazane was then mixed at a 3:1 mole ratio of endblocking triorganosilyl to total silicon-bonded hydroxyl radicals present in the resin copolymer and polydiorganosiloxane, and the mixture was allowed to react for 3 hours at 95°-100° C. The mixture was then heated to 140° C. and maintained at 140° C. under reflux conditions for 3 hours to remove condensation water.

Control PSA II is a pressure sensitive adhesive composition prepared by homogeneously mixing 60 parts of Resin A-1 with 40 parts of PDMS Fluid A and a fraction of a total of 2.4 parts of ammonium carbonate, heating the mixture to 100° C., and maintaining the temperature at 100° C. for 1 hour. Then the remaining fraction of the 2.4 parts ammonium carbonate were added to the mixture, and mixing continued for another hour at 100° C. The mixture was then stripped for 16 hours at 100° C. to remove the volatile components. Control PSA II was cooled to room temperature and was found to have (1) a specific gravity of 1.085–1.115, (2) a N.V.C. of at least 98.8%, where N.V.C. is defined as above, except that a 1 g. sample was used and the temperature of the oven was 177° C. and (3) a plasticity of $150-200 \times 10^{-3}$ inches as measured after a 24 hour rest and after force was applied on a 2 gram specimen for 3 minutes +/−5 seconds using ASTM D926.

Control PSA III was prepared by homogeneously mixing 26.74 parts of a hydroxy end blocked polydimethylsiloxane gum having a plasticity between 47 and 60 mils, 30.14 parts Resin A-2, 39.58 parts xylene, 3.40 parts isopropanol, and 0.14 parts of a mixture consisting of 9% tetramethylguanidine, 9% 2-ethyl hexanoic acid, and 82% xylene. The plasticity of the gum was measured at room temperature after force was applied on a 4.2 gram specimen for 3 minutes +/−5 seconds using ASTM D926. The homogeneous mixture was then stripped to remove the volatile components.

Preferably, the silicone pressure sensitive adhesives used in this invention have tack values ranging between about 50 and about 800 grams/cm$^2$; release values of less than or equal to 50 gm/cm; adhesion values of between about 100 and 2000 gm/cm; shear values between about 4 and 20 kg/6.25 cm$^2$; and a dynamic viscosity less than or equal to 800 poise on a 1 mm thick sample at temperatures of about 200° C.

A general method for measuring the values for tack, release and adhesion is described here. Although the following Examples utilize different chemical compositions, the same testing methods were followed for all samples. Measurements were obtained by testing a one inch wide polyester tape having a silicone pressure sensitive adhesive thereon. The adhesives were prepared by blending about 1.0 percent to 15.0 percent by weight of an organic wax with between 99.0 and 85.0 percent by weight of silicone pressure sensitive adhesive and casting it to about a 2 mil thickness on "SCOTCH-PAK" 1022 Release Liner, a polyester film coated with a release coating available from the 3M Company, St. Paul, Minnesota, owner of the trademark "SCOTCH-PAK", 3M Company Health Care Specialties Div. St. Paul Minnesota. After coating, "MYLAR" polyester film was adhered to each casted organic wax-containing sample with a 4 lb. rubber transfer roller. The laminate is then cut into one-inch wide strips with the use of a one-inch tape specimen cutter received from the Pressure Sensitive Tape Council, 1800 Pickwick Ave., Glenview, IL 60025-1357.

The tack values were measured using a "POLYKEN" Probe Tack Tester, Series 400, made by Testing Machines, Inc., Amityville, NY. The speed of the probe was controlled at 0.5 cm/second and 0.5 seconds dwell time. Our samples showed good results, as tack values of between about 50 and about 200 grams/cm$^2$ are considered acceptable. Test results for the tack values of these Examples for the various organic wax-containing adhesives are set forth in Tables 1A–3A.

The release values were obtained by stripping the tape from the "SCOTCH-PAK" 1022 Release Liner at a rate of 40 inches/minute at an angle of 180° while attached to a tensile testing machine. An average value over the entire length of the liner was recorded. The release values for each Example are set forth in Tables 1A–3A. Release values of less than 50 gm/cm are considered acceptable.

The adhesion values were obtained as follows. The tapes having the silicone pressure sensitive adhesive composition thereon were adhered to a stainless steel panel with a 4 lb. roller and allowed to rest for 20 minutes. The adhesion measurements were obtained by stripping each tape from the panel at a rate of 12 inches/minute at an angle of 180° while attached to a tensile testing machine. Results for our samples are in Tables 1A–3A. Desirable values range between about 100 and about 2000 gm/cm.

Shear values were measured by cutting three strips of the prepared laminates 2.5 cm wide and 7.5 cm in length. A 3.5 cm wide by 5.0 cm long strip of Mylar, a polyester film available from DuPont de Nemours, E. I. Co., Wilmington Delaware also owner of the trademark "Mylar", is applied to the adhesive strip so as to provide an overlap of 2.5 cm in the lengthwise direction. These are laminated using a 4 lb. rubber roller and allowed to equilibrate for 20 minutes. The specimen is mounted into the jaws of the Instron and pulled at a speed of 0.5 cm/min. and the peak load required to shear and separate the laminate is recorded in Kg/6.25 cm$^2$. Desirable values range between 4 and 20 Kg/6.25 cm$^2$.

Dynamic viscosities (n*) and elastic storage moduli (G') were measured on the adhesive compositions using a Rheometrics® Dynamic Spectrometer, Model RDS2, available from Rheometrics, Piscataway, NJ, and running a temperature sweep on 4 gram samples of 1 mm thickness, and operating the tester at a frequency of 100 radians/second and a 1% strain using a 50 mm cup and plate. Desirable values for dynamic viscosity are less than or equal to 800 poise at temperatures of about 200° C.

Elastic storage modulus is directly related to die swell and elastic memory. The higher the die swell, the smaller the size of an orifice required for a given coating thickness. Therefore, the lower the elastic storage modulus, the better, as it is then easier to coat onto a substrate. Tests similar to those run in these examples are described in ASTM 4065-82. Desirable storage modulus values should be less than or equal to 45,000 dynes/cm$^2$ at temperatures of about 200° C. or less.

Hereinbelow, the term "pressure sensitive adhesive" may be abbreviated to "PSA".

EXAMPLE 1

Adhesive formulations combining PSA I and amounts of organic waxes were prepared as set forth in Tables 1A and 1B. As shown in Table 1A, these adhesive preparations were evaluated for physical properties of tack, release, adhesion and shear. Tack values ranged between 86 and 341 gm/cm$^2$, and all were well within the acceptable range of 50 to 800 gm/cm$^2$. Release values ranged between 1.6 and 9.3 gm/cm. All samples were within the acceptable range of less than or equal to 50 gm/cm. Adhesion values for our samples ranged between 228 and 729 gm/cm. These values were all within the acceptable range of 100–2000 gm/cm. Shear values ranged from 12.06 to 16.06 Kg/6.25 cm$^2$ and were within the acceptable range of 4 to 20 kg/6.25 cm$^2$.

As shown in Table 1B, the Rheological properties of Elastic Modulus (G') and Dynamic Viscosity (n*) were evaluated for formulations of PSA I containing various organic waxes. Particularly relevant are the values measured at temperatures utilized in the hot-melt process below about 200° C. Desirable Elastic Modulus Values (G') were less than or equal to 45,000 dynes/cm$^2$ at 200° C.

The results displayed on Table 1B illustrate the overall desirable result of lowering viscosity of Adhesive I by adding the organic waxes, in comparison to Control PSA I without wax, at temperatures of 50° C., 125° C., 150° C. and 200° C.

Reduced dynamic viscosities were obtained at each tested temperature for 13 of the 18 wax-containing samples at 50° C. Reduced dynamic viscosity was achieved for all wax-containing samples at 125° C., 150° C., 175° C. and 200° C.

TABLE 1A

PHYSICAL PROPERTIES OF HOT MELT PSA-I WITH ORGANIC WAX ADDITIVES

| Additive$^a$ | Amount | Tack (gm/cm$^2$) | Release (gm/cm) | Adhesion (gm/cm) | Shear (kg/6.25 cm$^2$) |
|---|---|---|---|---|---|
| Control PSA-I | — | 284 | 2.7 | 729 | 16.67 |
| Ozokerite Sp1026 | 1% | 287 | 5.8 | 530 | 13.92 |
|  | 5% | 291 | 7.4 | 418 | 14.65 |
|  | 10% | 225 | 3.8 | 564 | 13.34 |
|  | 15% | 178 | 6.2 | 474 | 13.82 |
| Ozokerite 170D | 10% | 341 | 9.3 | 295 | 13.88 |
| Ozokerite 190 | 10% | 236 | 4.4 | 362 | 14.10 |
| Carnauba | 1% | 175 | 1.6 | 601 | 14.06 |
|  | 5% | 339 | 9.0 | 410 | 16.06 |
|  | 10% | 119 | 3.7 | 252 | 13.46 |
|  | 15% | 86 | 2.9 | 228 | 14.98 |
| Beeswax-Yellow | 10% | 229 | 6.2 | 411 | 14.16 |
| Beeswax-White | 10% | 336 | 5.4 | 415 | 12.06 |
| Ceresine Sp1022 | 1% | 286 | 3.6 | 723 | 13.53 |
|  | 5% | 229 | 4.3 | 428 | 13.35 |
|  | 10% | 327 | 8.4 | 341 | 13.98 |
|  | 15% | 252 | 5.1 | 506 | 14.61 |

TABLE 1A-continued

PHYSICAL PROPERTIES OF HOT MELT
PSA-I WITH ORGANIC WAX ADDITIVES

| Additive[a] | Amount | Tack (gm/cm$^2$) | Release (gm/cm) | Adhesion (gm/cm) | Shear (kg/6.25 cm$^2$) |
|---|---|---|---|---|---|
| Ceresine Sp252 | 10% | 159 | 6.3 | 550 | 13.17 |
| Candelilla | 10% | 125 | 1.8 | 330 | 15.06 |

[a]All additive waxes were purchased from Stahl and Pitsch Inc., West Babylon, N.Y.

TABLE 1B

RHEOLOGICAL PROPERTIES OF HOT MELT
PSA-I WITH ORGANIC WAX ADDITIVES

| Additive[a] | Amount | Values[b] | Temperature Sweep | | | | |
|---|---|---|---|---|---|---|---|
| | | | 50° C. | 125° C. | 150° C. | 175° C. | 200° C. |
| Control PSA-I | — | G' | 6.7E5[c] | 2.7E5 | 1.7E5 | 9.8E4 | 4.9E4 |
| | | n* | 6.8E3 | 3.3E3 | 2.2E3 | 1.4E3 | 8.1E2 |
| Ozokerite Sp1026 | 1% | G' | 6.6E5 | 1.4E5 | 7.5E4 | 3.9E4 | — |
| | | n* | 6.7E3 | 1.9E3 | 1.2E3 | 6.4E2 | — |
| | 5% | G' | 6.3E5 | 2.1E4 | 8.1E3 | 4.4E3 | — |
| | | n* | 6.4E3 | 3.5E2 | 1.7E2 | 1.5E2 | — |
| | 10% | G' | 6.7E5 | 6E4 | 2.7E4 | 1.5E4 | 3.9E3 |
| | | n* | 6.8E3 | 8.9E2 | 4.7E2 | 3E2 | 1.2E2 |
| | 15% | G' | 6.5E5 | 3.8E4 | 1.1E2 | 3.4E3 | — |
| | | n* | 6.6E3 | 6.3E2 | 2.3E2 | 1E3 | — |
| Ozokerite 170D | 10% | G' | 6.8E5 | 5.3E3 | 1.8E3 | 7.4E2 | — |
| | | n* | 6.9E3 | 9.9E1 | 4.2E1 | 2.2E1 | — |
| Ozokerite 190 | 10% | G' | 6.4E5 | 4.8E4 | 2.5E4 | 1.3E4 | — |
| | | n* | 6.5E3 | 7.4E2 | 4.4E2 | 2.8E2 | — |
| Carnauba Wax | 1% | G' | 6.8E5[c] | 2.4E5 | 1.5E5 | 7.9E4 | 4.5E4 |
| | | n* | 6.9E3 | 3E3 | 2E3 | 1.2E3 | 7.5E2 |
| | 10% | G' | 6.5E5 | 1.2E5 | 3.4E4 | 1.3E4 | 5.3E3 |
| | | n* | 6.6E3 | 1.6E3 | 5.4E2 | 2.4E2 | 1.1E2 |
| | 15% | G' | 4.7E5 | 5.3E4 | 2E4 | 6.2E3 | 2.2E3 |
| | | n* | 4.7E3 | 7.8E2 | 3.1E2 | 1.1E2 | 4.8E1 |
| Beeswax Yellow | 10% | G' | 6.3E5 | 1E5 | 5.8E4 | 3.1E4 | 1.5E4 |
| | | n* | 6.5E3 | 1.4E3 | 8.8E2 | 5.5E2 | 3.2E2 |
| Beeswax White | 10% | G' | 6E5 | 9.7E4 | 5.5E4 | 3.2E4 | 1.6E4 |
| | | n* | 6.2E3 | 1.5E3 | 8.6E2 | 5.7E2 | 3.3E2 |
| Ceresine Sp1022 | 1% | G' | 6.5E5 | 2E5 | 1.2E5 | 7.4E4 | 4.1E4 |
| | | n* | 6.6E3 | 2.5E3 | 1.6E3 | 1E3 | 6.8E2 |
| | 5% | G' | 6.7E5[c] | 6.6E4 | 2E4 | 2.3E4 | 1.4E4 |
| | | n* | 6.8E3 | 1E3 | 6.7E2 | 4.5E2 | 3.1E2 |
| | 10% | G' | 5.9E5 | 1.7E4 | 1.2E4 | 5.9E3 | — |
| | | n* | 6.1E3 | 2.7E2 | 1.9E2 | 8.5E1 | — |
| | 15% | G' | 5.4E5 | 2.1E4 | 1.6E4 | 8.4E3 | 2.2E3 |
| | | n* | 5.4E3 | 3.1E2 | 2.2E2 | 1.2E2 | 3.7E1 |
| Ceresine Sp252 | 10% | G' | 5.9E5 | 2.5E4 | 1.4E4 | 7.7E3 | 5E3 |
| | | n* | 6.1E3 | 4.8E2 | 2.8E2 | 2E2 | 1.5E2 |
| Candelilla | 10% | G' | 6.1E5 | 8.9E4 | 4.6E4 | 2.3E4 | 1.1E4 |
| | | n* | 6.3E3 | 1.2E3 | 7.4E2 | 4.2E2 | 2.4E2 |

[a]All additive waxes were purchased from Stahl and Pitsch Inc., West Babylon, N.Y.
[b]Values for Elastic Modulus (G') in dynes/cm$^2$ units and Dynamic Viscosity (n*) in poise units.
[c]E indicates exponential value, e.g. 6.7E5 means 6.7 × 10$^5$, and the other values are likewise interpreted.

EXAMPLE 2

Adhesive formulations combining Control PSA II with varying amounts of organic waxes were prepared as set forth in Tables 2A and 2B. As shown in Table 2A, these adhesive preparations were evaluated for physical properties of tack, release, adhesion and shear. Tack values for all samples were outside the acceptable range of 50 to 2000 gm/cm$^2$. Release values ranged between 0 and 0.8 gm/cm. All samples were within the acceptable release value range of less than or equal to 50 gm/cm. All samples were within the acceptable range for adhesion values of 100–2000 gm/cm$^2$. All samples had shear values within the acceptable range of 4 to 20 kg/6.25 cm$^2$.

As shown in Table 2B, the Rheological properties of Elastic Modulus (G') and Dynamic Viscosity (n*) were evaluated for the various adhesive formulations. Particularly relevant are the values measured at temperatures equal to or below 200° C. Elastic Modulus Values (G') equal to or less than 45,000 dynes/cm$^2$ at 200° C. were desirable. Eight of ten samples had values within the acceptable range.

Table 2B illustrates the desirable result of lowering the dynamic viscosity of Control PSA II formulated with an organic wax, in comparison to Control PSA II without wax, at temperatures of 50° C., 125° C., 150° C. and 200° C.

Reduced dynamic viscosity was obtained for six of the ten wax-containing samples at 50° C. Reduced dynamic viscosity was achieved for all wax-containing samples at 125° C.; nine of ten samples at 150° C.; eight of ten samples at 175° C.; and eight of ten samples at 200° C.

TABLE 2A
PHYSICAL PROPERTIES OF HOT MELT PSA-II WITH ORGANIC WAX ADDITIVES

| Additive[a] | Amount | Tack (gm/cm$^2$) | Release (gm/cm) | Adhesion (gm/cm) | Shear (kg/6.25 cm$^2$) |
|---|---|---|---|---|---|
| Control PSA-I | — | <50 | 0.8 | 876 | 14.60 |
| Ozokerite Sp1026 | 10% | 0 | 0.0 | 440 | 16.21 |
| Carnuba | 1% | 0 | 0.0 | 529 | 16.06 |
|  | 5% | 0 | 0.1 | 269 | 14.02 |
|  | 10% | 0 | 0.4 | 174 | 15.18 |
|  | 15% | 0 | 0.2 | 75 | 14.46 |
| Ceresine Sp1022 | 1% | 0 | 0.0 | 609 | 14.27 |
|  | 5% | 0 | 0.5 | 585 | 16.87 |
|  | 10% | 32 | 0.8 | 566 | 15.32 |
|  | 15% | 0 | 0.4 | 628 | 13.64 |

[a]All additive waxes were purchased from Stahl and Pitsch, Inc., West Babylon, N.Y.

TABLE 2B
RHEOLOGICAL PROPERTIES OF HOT MELT PSA-II WITH ORGANIC WAX ADDITIVES

| Additive[a] | Amount | Values[b] | 50° C. | 125° C. | 150° C. | 175° C. | 200° C. |
|---|---|---|---|---|---|---|---|
| Control PSA-I | — | G' | 6.7E5[c] | 3.7E5 | 2.1E5 | 1.1E5 | 6.4E4 |
|  |  | n* | 6.9E3 | 4.3E3 | 3E3 | 1.7E3 | 9.8E2 |
| Ozokerite Sp1026 | 10% | G' | 6E5 | 1.4E5 | 6.4E4 | 2.7E4 | 1.4E4 |
|  |  | n* | 6.2E3 | 1.9E3 | 8.1E2 | 4.3E2 | 2.4E2 |
| Carnauba | 1% | G' | 6.9E5 | 4.2E5 | 2.8E5 | 1.7E5 | 1.3E5 |
|  |  | n* | 6.9E3 | 4.7E3 | 3.3E3 | 2.2E3 | 1.7E3 |
|  | 5% | G' | 6.7E5 | 2.1E5 | 1.2E5 | 6.9E4 | — |
|  |  | n* | 6.8E3 | 2.6E3 | 1.6E3 | 9.9E2 | — |
|  | 10% | G' | 7E5 | 2.7E5 | 1.4E5 | 7.8E4 | 4.4E4 |
|  |  | n* | 7.1E3 | 3.3E3 | 1.8E3 | 1E3 | 7.2E2 |
|  | 15% | G' | 3.2E5 | 2.3E5 | 8.1E4 | 1.5E4 | 5.6E3 |
|  |  | n* | 3.3E3 | 2.7E3 | 1.1E3 | 2.5E2 | 9.7E1 |
| Ceresine Sp1022 | 1% | G' | 6.8E5 | 3.8E5 | 2.2E5 | 1.4E5 | 7.7E4 |
|  |  | n* | 6.9E3 | 4.3E3 | 2.7E3 | 1.8E3 | 1.1E3 |
|  | 5% | G' | 3.5E5[c] | 1.4E5 | 6.8E4 | 3.2E4 | 1.9E4 |
|  |  | n* | 3.9E3 | 1.8E3 | 9.2E2 | 5.1E2 | 3.2E2 |
|  | 10% | G' | 5.5E5 | 1.3E5 | 8.7E4 | 5E4 | 2.8E4 |
|  |  | n* | 5.7E3 | 1.7E3 | 1.2E3 | 7.5E2 | 4.7E2 |
|  | 15% | G' | 6.4E5 | 8.5E4 | 4.9E4 | 3.3E4 | 2.4E4 |
|  |  | n* | 6.5E3 | 1.2E3 | 6.3E2 | 4.3E2 | 3.2E2 |
| Candelilla | 10% | G' | 6.1E5 | 8.9E4 | 4.6E4 | 2.3E4 | 1.1E4 |
|  |  | n* | 6.3E3 | 1.2E3 | 7.4E2 | 4.2E2 | 2.4E2 |

[a]All additive waxes were purchased from Stahl and Pitsch Inc., West Babylon, N.Y.
[b]Values for Elastic Modulus (G') in dynes/cm$^2$ units and Dynamic Viscosity (n*) in poise units.
[c]E indicates exponential value, e.g. 6.7E5 means 6.7 × 10$^5$, and the other values are likewise interpreted.

EXAMPLE 3

Now we look at adhesive formulations combining Control PSA III with varying amounts of organic waxes which were prepared as set forth in Tables 3A and 3B. As shown in Table 3A, these adhesive preparations were evaluated for physical properties of tack, release, adhesion and shear. Tack values ranged between 97 and 371 gm/cm$^2$ were well within the acceptable range of 50 to 800 gm/cm$^2$. Release values ranged between 1.2 and 16.1 gm/cm. All samples were within the acceptable range of less than or equal to 50 gm/cm. Adhesion values ranged between 134 and 683 gm/cm. All samples were within the acceptable adhesion range of 100–2000 gm/cm. Shear values ranged from 12.81 to 15.91 kg/6.25 cm$^2$ and were within the acceptable range of 4 to 20 kg/6.25 cm$^2$.

As shown in Table 3B, the Rheological properties of Elastic Modulus (G') and Dynamic Viscosity (n*) were evaluated for the various adhesive formulations. Particularly relevant are the values measured at temperatures equal to or less than 200° C. Elastic Modulus Values (G') exceeded the desirable range of less than or equal to 45,000 dynes/cm$^2$ at 200° C.

As shown in Table 3B reduced dynamic viscosity was achieved for five of nine wax-containing samples at 125° C., seven of nine samples at 150° C. and five of nine samples at 175° C. Dynamic viscosity increased at 200° C. for all samples. At 200° C. the dynamic viscosity values were outside the desirable range of less than or equal to 800 poise at 200° C.

TABLE 3A
PHYSICAL PROPERTIES OF HOT MELT PSA-II WITH ORGANIC WAX ADDITIVES

| Additive[a] | Amount | Tack (gm/cm$^2$) | Release (gm/cm) | Adhesion (gm/cm) | Shear (kg/6.25 cm$^2$) |
|---|---|---|---|---|---|
| Control PSA-I | — | 253 | 3.0 | 683 | 18.38 |
| Ozokerite Sp1026 | 10% | 271 | 7.6 | 535 | 13.53 |
| Carnuba | 1% | 242 | 8.4 | 658 | 13.19 |
|  | 5% | 187 | 16.1 | 335 | 14.44 |

TABLE 3A-continued

PHYSICAL PROPERTIES OF HOT MELT PSA-II WITH ORGANIC WAX ADDITIVES

| Additive[a] | Amount | Tack (gm/cm$^2$) | Release (gm/cm) | Adhesion (gm/cm) | Shear (kg/6.25 cm$^2$) |
|---|---|---|---|---|---|
| | 10% | 196 | 3.3 | 404 | 15.91 |
| | 15% | 97 | 1.2 | 134 | 12.81 |
| Ceresine Sp1022 | 1% | 147 | 4.8 | 447 | 14.95 |
| | 5% | 198 | 15.5 | 509 | 13.86 |
| | 10% | 371 | 8.7 | 433 | 13.61 |
| | 15% | 154 | 11.6 | 340 | 13.46 |

[a]All additive waxes were purchased from Stahl and Pitsch, Inc., West Babylon, N.Y.

TABLE 3B

RHEOLOGICAL PROPERTIES OF HOT MELT PSA-III WITH ORGANIC WAX ADDITIVES

| Additive[a] | Amount | Values[b] | 50° C. | 125° C. | 150° C. | 175° C. | 200° C. |
|---|---|---|---|---|---|---|---|
| Control PSA-I | — | G' | 5E5[c] | 3.5E5 | 3E5 | 2.6E5 | 1.5E5 |
| | | n* | 5.1E3 | 3.8E3 | 3.2E3 | 2.7E3 | 1.9E2 |
| Ozokerite Sp1026 | 10% | G' | 6.3E5 | 1.9E5 | 1.5E5 | 1.1E5 | — |
| | | n* | 6.4E3 | 2.1E3 | 1.8E3 | 1.4E3 | — |
| Carnauba | 1% | G' | 6.7E5 | 4.3E5 | — | — | — |
| | | n* | 6.8E3 | 4.5E3 | — | — | — |
| | 5% | G' | 6.7E5 | 4.3E5 | 3.7E5 | 3.2E5 | 2.7E5 |
| | | n* | 6.8E3 | 4.5E3 | 3.8E3 | 3.3E3 | 2.9E3 |
| | 10% | G' | 6.8E5 | 3.1E5 | 2.9E5 | 2.7E5 | — |
| | | n* | 6.9E3 | 3.3E3 | 3E3 | 2.9E3 | — |
| | 15% | G' | 6.3E5 | 4.1E5 | 3.5E5 | 3.1E5 | 2.6E5 |
| | | n* | 6.4E3 | 4.2E3 | 3.6E3 | 3.2E3 | 2.8E3 |
| Ceresine Sp1022 | 1% | G' | 6E5[c] | 3.4E5 | 2.7E5 | 2.2E5 | — |
| | | n* | 6.1E3 | 3.2E3 | 2.9E3 | 2.4E3 | — |
| | 5% | G' | 5.6E5 | 2.1E5 | 1.7E5 | 1.2E5 | — |
| | | n* | 5.8E3 | 2.4E3 | 1.9E3 | 1.5E3 | — |
| | 10% | G' | 5E5 | 1.9E5 | 1.4E5 | 1E5 | 7.6E4 |
| | | n* | 5.2E3 | 2.1E3 | 1.7E3 | 1.2E3 | 9.9E2 |
| | 15% | G' | 6.3E5 | 1.4E5 | 1.2E5 | 8.9E4 | 6.4E4 |
| | | n* | 6.5E3 | 1.9E3 | 1.5E3 | 1.1E3 | 9E2 |

[a]All additive waxes were purchased from Stahl and Pitsch Inc., West Babylon, N.Y.
[b]Values for Elastic Modulus (G') in dynes/cm$^2$ units and Dynamic Viscosity (n*) in poise units.
[c]E indicates exponential value, e.g. 6.7E5 means 6.7 × 10$^5$, and the other values are likewise interpreted.
G' = Elastic Modulus, dynes/cm$^2$
n* = Dynamic viscosity, poise
E = Exponential value (e.g. 1.9E3 = 1.9 × 10$^3$)
Temperature Sweep - Pheometrics RDSII
50 mm cup and plate
4 gram sample
1 mm thickness
100 radian/second
1% strain

I claim:

1. A matrix transdermal drug delivery device for a bioactive agent, comprising:
   (a) a backing substrate;
   (b) an adhesive matrix atop at least portions of said backing substrate, said adhesive matrix formed of a non-flammable, hot-melt, silicone pressure sensitive adhesive composition having tackiness and adhesiveness containing (i) between about 30 and about 70 percent by weight of a benzene-soluble resinous copolymer containing silicon-bonded hydroxyl radicals and consisting essentially of triorganosiloxy units of the formula R$_3$SiO$_{\frac{1}{2}}$ and tetra functional siloxy units of the formula SiO$_{4/2}$ in a ratio of about 0.6 to 0.9 triorganosiloxy units for each tetra functional siloxy unit present in the copolymer, wherein each R is a monovalent organic radical independently selected from the group consisting of hydrocarbon radicals of from 1 to 6 inclusive carbon atoms; (ii) between about 22 and about 60 percent by weight of a polydimethylsiloxane fluid; and (iii) between about 1.0 and about 25 percent by weight of an organic wax, all weight percents being based on total composition weight, said wax having a melting point of between about 30° C. and about 150° C., and said organic wax decreasing the dynamic viscosity of the resultant hot-melt silicone pressure sensitive adhesive at temperatures ranging up to about 200° C., and said silicone pressure sensitive adhesive composition including ingredients selected from the group consisting of drugs, excipients, co-solvents, enhancers, and mixtures thereof where the silicone pressure sensitive adhesive composition is compatible with said drugs, excipients, co-solvents and enhancers wherein the silicone pressure sensitive adhesive composition has a tack value between about 50 and 800 g/cm$^2$ measured using a probe tack tester at a speed of 0.5 cm/second with a 0.5 second dwell time; and
   (c) a release liner contacted on the adhesive matrix.

2. A reservoir transdermal drug delivery device, comprising:
   (a) a backing substrate;
   (b) a reservoir attached to at least portions of the backing substrate, said reservoir containing compositions selected from the group consisting of drugs, excipients, co-solvents, enhancers, and mixtures thereof;

(c) a non-flammable hot-melt silicone pressure sensitive adhesive composition having tackiness and adhesiveness containing (i) between about 30 and about 70 percent by weight of a benzene-soluble resinous copolymer containing silicon-bonded hydroxyl radicals and consisting essentially of triorganosiloxy units of the formula $R_3SiO_{\frac{1}{2}}$ and tetra functional siloxy units of the formula $SiO_{4/2}$ in a ratio of about 0.6 to 0.9 triorganosiloxy units for each tetra functional siloxy unit present in the copolymer, wherein each R is a monovalent organic radical independently selected from the group consisting of hydrocarbon radicals of from 1 to 6 inclusive carbon atoms; (ii) between about 22 and about 60 percent by weight polydimethylsiloxane fluid; and (iii) between about 1.0 and about 25 percent by weight of an organic wax, all weight percents being based on total composition weight, said wax having a melting point of between about 30° C. and about 150° C., and said wax decreasing dynamic viscosity of the hot-melt silicone pressure sensitive adhesive at temperatures ranging up to about 200° C., wherein the silicone pressure sensitive adhesive composition has a tack value between about 50 and 800 g/cm$^2$ measured using a probe tack tester at a speed of 0.5 cm/second with a 0.5 second dwell time, coated on top of the reservoir and portions of the backing substrate not covered by the reservoir; and (d) a release liner attached to the silicone pressure sensitive adhesive.

3. The matrix transdermal drug delivery device for a bioactive agent of claim 1, wherein the organic wax is selected from the group consisting of naturally occurring waxes including carnauba, candelilla, beeswax, paraffin, ozokerite, ceresine waxes, and mixtures thereof.

4. The matrix transdermal drug delivery device for a bioactive agent of claim 1, wherein the organic wax is present in an amount between about 5 percent and about 20 percent by weight based on total adhesive composition weight.

5. The matrix transdermal drug delivery device for a bioactive agent of claim 1, wherein the silicone pressure sensitive adhesive containing the organic wax has a dynamic viscosity of less than or equal to 800 poise at a temperature of about 200° C.

6. The reservoir transdermal drug delivery device of claim 2, wherein the organic wax is selected from the group consisting of naturally occurring waxes including carnauba, candelilla, beeswax, paraffin, ozokerite, ceresine waxes, and mixtures thereof.

7. The reservoir transdermal drug delivery device of claim 2, wherein the organic wax is present in an amount between about 5 percent and about 20 percent by weight based on total adhesive composition weight.

8. The reservoir transdermal drug delivery device of claim 2, wherein the silicone pressure sensitive adhesive containing the organic wax has a dynamic viscosity of less than or equal to 800 poise at a temperature of about 200° C.

9. The matrix transdermal drug delivery device of claim 1, wherein the silicone pressure sensitive adhesive composition has an adhesion value between about 100 and 2000 gm/cm determined by first adhering tape having the silicone pressure sensitive adhesive composition thereon to stainless steel using a 4 pound roller and, subsequently, stripping the tape from the stainless steel while pulling at a rate of 12 inches/minute at an angle of 180° using a tensile testing machine.

10. The reservoir transdermal drug delivery device of claim 2, wherein the silicone pressure sensitive adhesive composition has an adhesion value between about 100 and 2000 gm/cm determined by first adhering tape having the silicone pressure sensitive adhesive composition thereon to stainless steel using a 4 pound roller and, subsequently, stripping the tape from the stainless steel while pulling at a rate of 12 inches/minute at an angle of 180° using a tensile testing machine.

* * * * *